United States Patent [19]

McGinley et al.

[11] Patent Number: 4,518,433
[45] Date of Patent: May 21, 1985

[54] ENTERIC COATING FOR PHARMACEUTICAL DOSAGE FORMS

[75] Inventors: Emanuel J. McGinley, Morrisville; Domingo C. Tuason, Jr., Bensalem, both of Pa.

[73] Assignee: FMC Corporation, Philadelphia, Pa.

[21] Appl. No.: 440,118

[22] Filed: Nov. 8, 1982

[51] Int. Cl.$^3$ ............... C08L 1/08; C08G 18/10
[52] U.S. Cl. .................. 106/180; 106/198; 264/12; 524/312; 536/64; 536/76
[58] Field of Search .............. 106/180, 198; 424/3, 424/35; 536/38, 76, 64; 264/12, 13; 524/312

[56]  References Cited
U.S. PATENT DOCUMENTS

| | | | |
|---|---|---|---|
| 2,740,723 | 4/1956 | Voris | 106/196 |
| 2,800,463 | 7/1957 | Morrison | 523/309 |
| 2,843,582 | 7/1958 | Voris | 106/198 |
| 2,843,583 | 7/1958 | Voris | 536/38 |
| 3,539,365 | 10/1970 | Durand et al. | 106/197 |
| 3,725,089 | 4/1973 | Zola | 106/170 |
| 3,779,783 | 12/1973 | Bunger et al. | 106/171 |
| 3,935,326 | 1/1976 | Groppenbacker et al. | 427/3 |
| 3,983,263 | 9/1976 | Weiss et al. | 524/312 |
| 4,112,215 | 9/1978 | Boessler | 528/503 |
| 4,177,177 | 12/1979 | Vanderhoff et al. | 106/70 |
| 4,223,008 | 9/1980 | Gregory | 424/32 |
| 4,287,221 | 9/1981 | Tonedachi et al. | 424/35 |
| 4,330,338 | 5/1982 | Banker | 106/197 |
| 4,340,582 | 7/1982 | Kriesel | 424/35 |
| 4,385,078 | 5/1983 | Onda | 106/170 |

Primary Examiner—Theodore Morris
Attorney, Agent, or Firm—C. H. Johnson; C. Egolf

[57] ABSTRACT

The application discloses a process for making a polymeric powder which is readily dispersible in water to provide a composition useful for forming an enteric coating on pharmaceutical dosage forms and also a process for using the powder for its intended purpose.

22 Claims, No Drawings

ENTERIC COATING FOR PHARMACEUTICAL DOSAGE FORMS

This invention relates to a polymeric powder which is readily dispersible in water to make a composition useful for providing enteric coatings on pharmaceutical dosage forms such as tablets, pills, capsules, powders, granules and beads. More particularly, the invention relates to such a polymeric powder wherein very small spherical powder particles are adhered together in aggregates which when stirred in water with mild agitation readily break up and allow the individual particles to disperse. The invention also relates to a process for making such a powder and to a process for utilizing the same.

As used herein the term "polymeric powder" means a powder the individual particles of which are aggregates of spherical polymer particles providing enteric functionality but which aggregates may also comprise other ingredients such as plasticizer, emulsifying agent and/or a dispersion stabilizer, color, etc. Such aggregates are referred to herein as "powder particles".

Pharmaceutical dosage forms such as tablets and the like commonly consist of a core containing one or more pharmacologically active ingredients together with various excipients which serve as binding agents, disintegrants, etc. The core may be provided with some form of a coating which may serve a variety of purposes such as rendering the dosage more palatable, improving the appearance, ease of identification, or for controlling release of the active ingredient both as to time and place. Coatings which are insoluble in the gastric juices of the stomach but which dissolve in the alkaline environment of the intestines are known and are needed for a variety of medical reasons not germane to the present invention. Such coatings are variously referred to as enteric coatings or enterosoluble coatings and will be so referred to hereinafter.

There are a number of known enteric materials, the most widely used probably being cellulose acetate phthalate and it is with this polymer that the present invention is particularly concerned. While being water-insoluble, cellulose acetate phthalate is readily soluble in volatile organic solvents such as acetone, and mixtures of acetone and methanol, acetone and methylene chloride, etc. and until fairly recently coating compositions were formed by dissolving the polymer in organic solvent. This practice of forming a coating composition by dissolving a polymer in organic solvent has also been used with water-insoluble non-enteric polymers such as ethyl cellulose. To the solution are frequently added pigments, surfactants, plasticizers, preservatives, flavors, etc. and the final composition is sprayed or otherwise applied to the dosage form so as to provide a continuous film upon evaporation of the solvent.

There were and are serious problems in using a solvent system for coating tablets and the like. Often the vapors of organic solvents are toxic or flammable and provide a hazard to the operator and to the premises where the coating operation is performed. There are also environmental problems necessitating the use of extensive recovery systems to avoid escape of the vapors into the atmosphere.

Within recent years aqueous coating systems (as opposed to organic solvent systems) have been developed to eliminate the above mentioned and other problems connected with solvent systems. In one of these newer systems water-insoluble polymer particles are dispersed in water to form a pseudolatex coating composition which is applied to the dosage form in any of several known procedures, usually by spraying. A plasticizer is usually incorporated into the dispersion and often a pigment and other materials are added. As the water evaporates, usually being aided by the controlled application of heat, the polymer particles coalesce to form a continuous film coating.

One of the problems that delayed the development of an aqueous system was in producing polymer particles of a size sufficiently small as to form a stable dispersion; that is to say so that the particles will remain suspended in water due to their Brownian motion and/or convection currents, rather than settle out due to gravity. While reasonably good continuous films may be formed from aqueous polymeric compositions having polymer particles up to about 5.0 $\mu$m in greatest dimension, as a general rule the smaller the size of the polymer particles, the better the film. To form a stable dispersion it is essential that the polymer particles be no more than about 0.5 $\mu$m in greatest dimension and for both best dispersion stability and best film forming properties it is desirable that the polymer particles be spherical and between 0.2 and 0.5 $\mu$m in diameter.

Presently known techniques for mechanical particle size reduction have not been successful in producing polymer particles of the preferred size range. There are known emulsion polymerization techniques for forming dispersions having particles of the desired size but these techniques leave potentially physiologically harmful residual monomer in the dispersion and are therefore not entirely satisfactory when the dispersion is to be used for coating pharmaceutical or food products. Moreover, the most desirable enteric coatings are composed of polymers such as cellulose acetate phthalate which are incapable of being emulsion polymerized.

To avoid the problems associated with emulsion polymerization, aqueous polymer dispersions having the requisite particle size and form can be made by dissolving the polymer in a water immiscible organic solvent, and emulsifying the organic solution in water containing at least one nonionic, anionic or cationic emulsifying agent. The crude emulsion is then subjected to comminuting forces sufficient to form a colloidal or near colloidal dispersion of small, even sized spherical polymer particles having a diameter of less than 1.0 $\mu$m, preferably between 0.2 and 0.5 $\mu$m. The organic solvent is stripped from the system by distillation. For more details as to a process for making such a polymer emulsion or dispersion, reference is directed to U.S. Pat. No. 4,177,177 to Vanderhoff et al. The actual method of forming the dispersion is not a part of the present invention and methods other than that described in the Vanderhoff et al. patent may be used, so long as the desired polymer particle size and shape is obtained. U.S. Pat. No. 4,330,338 to Banker teaches the use of aqueous dispersions of various polymers including cellulose acetate phthalate for forming coatings on pharmaceutical dosage forms.

Applicants have found that while aqueous dispersions of some polymers such as ethyl cellulose are chemically stable for relatively long periods of time, perhaps indefinitely, dispersions of cellulose acetate phthalate are not. The presence of water in the dispersion hydrolyzes the cellulose acetate phthalate and gradually increases the phthalic acid content to beyond acceptable limits for pharmaceutical use. This inability to successfully store cellulose acetate phthalate aqueous dispersions for long periods of time also applies for the same reason to aqueous dispersions of such other known enteric polymers as hydroxypropyl methylcellulose phthalate and polyvinyl acetate phthalate. Not being able to successfully store the polymer dispersion is particularly undesirable in view of the fact that the scale on which the dispersions are typically used is significantly smaller than the scale on which they can be economically manufactured.

Since it is the presence of water that causes the phthalic acid content of the cellulose acetate phthalate to increase with the passage of time, the storage problem may be overcome by having the cellulose acetate phthalate particles in dry powder form, rather than being dispersed in water. Not only is the dry powder chemically stable but it is considerably easier and less expensive to ship than an aqueous dispersion. In addition, the dry powder is less susceptible to harmful effects of extremes of temperature and less susceptible to microbial growth. However, getting from an aqueous dispersion of the polymer particles to a dry powder which can be reconstituted in water to the preferred particle size range is not a simple matter. As mentioned above, when water is evaporated from the dispersion by any method, the particles coalesce and form a continuous film. This coalescence of the particles of course will occur regardless of the nature of the substrate, if any, from which the water is evaporated. Once the particles have coalesced there is no known way that the coalesced particles can be separated and restored to the submicron spherical size that they had while in dispersion.

According to U.S. Pat. No. 3,539,365 to Durand et al., an aqueous dispersion of non-water soluble beta-1,4 glucan particles of less than 1.0 µm in greatest dimension are spray dried after first being coated while in dispersion with a water soluble barrier material. Without the barrier the beta-1,4 glucan particles would bond together in aggregates which are too tightly bonded to be redispersed as stable dispersions. The barrier material surrounding each particle prevents direct contact between the beta-1,4 glucan particles and avoids the undesirable aggregation of particles. The spray dryed particles may be readily redispersed in water to form a stable dispersion. The Durand et al. patent mentions a number of more or less useful barrier materials, all of which are water soluble. The amount and type of water soluble barrier materials described by Durand et al would interfere with the enteric performance of coating compositions of enterosoluble polymers dried by this method.

U.S. Pat. No. 2,800,463 to Morrison describes a process for converting an aqueous polyvinyl acetate emulsion containing emulsifying agents or protective colloids like polyvinyl alcohol, gum tragacanth, gum acacia, etc. into a powder capable of being redispersed in water. As described, the process involves either spray drying or freeze drying. The spray drying is carried out at temperatures below that at which the polymer particles sinter together. The dried powder is described as being useful in various ways such as for manufacture of paint and adhesives. There is no suggestion that the powder be used to make a composition useful for coating pharmaceutical dosage forms.

According to U.S. Pat. No. 4,112,215 to Boessler et al., a dry powder of a polymeric material suitable for use in a solvent coating composition for pharmaceutical dosage forms may be produced by spray drying an aqueous dispersion of certain vinyl copolymers. The spray drying is carried out at a temperature such that the vinyl copolymer particles do not exceed the minimum film-forming temperature of the polymer. This method requires very careful control of the temperature of the air in the spray dryer. As pointed out in said U.S. Pat. No. 4,112,215, the actual air temperature must be chosen depending upon the amount of water in the dispersion as well as upon the known film-forming temperature of the polymer. Other factors not mentioned in the patent but which affect the heating of the polymer particles are the temperature of the water in the dispersion and the size of the particles. As pointed out in the patent, the only way of knowing whether the proper air temperature is used is by examination of the product obtained after completion of the drying operation; obviously not a very desirable circumstance.

There are also other known methods of making polymeric powders capable of being dispersed in water to form film-forming coating compositions. However, so far as applicants are aware, none of the prior processes result in a powder wherein the individual polymer particles are adhered together in aggregates which when stirred in water with mild agitation readily break up and allow the individual particles to disperse. The present invention does provide such aggregates and as will later be more fully described such aggregates of particles facilitate collection of the powder and also facilitate dispersion of the powder.

According to the present invention, the aqueous dispersion of substantially spherical cellulose acetate phthalate particles of less than 5.0 µm diameter, preferably of a diameter between about 0.2 to 0.5 µm, optionally formed as above described in reference to the patent to Vanderhoff et al. U.S. Pat. No. 4,177,177, is spray dried after having had added thereto a water insoluble barrier material which minimizes contact and coalescence of the cellulose acetate phthalate particles. As previously mentioned, the purpose of the powder formed by spray drying the dispersion is for redispersion in water to form a composition suitable for use in providing an enteric coating on pharmaceutical dosage forms. It has been found that when water soluble barrier materials such for example as the sodium carboxy methyl cellulose of the Durand et al. U.S. Pat. No. 3,539,365 is used in a sufficient quantity to prevent coalescence of the cellulose acetate phthalate particles, the enteric properties of films produced are adversely affected and the coated tablet will not pass the United States Pharmacopia (U.S.P.) XX Enteric Disintegration Test.

While there may be a number of suitable barrier materials useful with various specific enterosoluble polymers, one which has been found satisfactory for use with cellulose acetate phthalate is an acetylated monoglyceride characterized by being liquid at room temperature and having a degree of acetylation of at least about 96%. This material is water insoluble and oily in nature. It may be added directly to the cellulose acetate phthalate aqueous dispersion but preferably the oily material is pre-emulsified in water and the emulsion is then added and mixed with the dispersion. The use level of this barrier material which has been found to be effective is between 6% and 18% based upon the weight of the dry insoluble solids contained in the dispersion. Levels below 6% are not sufficient to prevent coalescence of large numbers of polymer particles. Even at the 6-18% level there is some coalescence of polymer particles but not to an extent that reconstitution of the powder particles is substantially different from the original dispersion particle size. This particular acetylated monoglyceride is also a plasticizer for cellulose acetate phthalate and at use levels above about 18% the plasticizing action results in premature coalescence during the spray drying operation due to the softening of the primary polymer particles. Also, levels above about 18% cause powder oiliness and an excessive wall build up in the dryer. The preferred level of use of the barrier material is between 10 and 14%.

While the acetylated monoglyceride has been referred to herein as a barrier material, the mechanism of its operation is not fully understood. The acetylated monoglyceride exists in the water phase of the dryer feed slurry in a finely divided emulsion form homogeneously mixed with the insoluble cellulose acetate phthalate dispersion. Upon flash evaporation of the water, results indicate that the emulsion droplets of the acetylated monoglyceride prevent or impede direct contact between the cellulose acetate phthalate polymer particles. Furthermore, it is believed that these oily droplets upon removal of the water phase are deposited on and wet the surface of the polymer particles and in fact partially plasticize the particles. The oily liquid acetylated monoglyceride remains unchanged at various temperatures encountered in the spray drying process and as the powder dries it serves as an adhesive to form small aggregates of adhered uncoalesced particles of cellulose acetate phthalate. These aggregates, though small, are considerably larger than the individual polymer particles and are much easier to collect from the spray dryer. The individual particles are so small that they tend to float in air and do not readily drop into the collecting area of the dryer. In normal spray drying operations, the small individual particles would be referred to as "fines" and would be permitted to pass out of the product collection chamber and some special means would be provided for capturing them. The powder thus formed is chemically and physically stable thus permitting long term storage. The addition of the barrier material and subsequent spray drying must of course be done before the aforementioned hydrolysis raises the phthalic acid content to beyond acceptable limits, defined by U.S.P. XX to be 6% by weight of the polymer. The expression "freshly prepared" is used hereinafter in reference to the aqueous dispersion of a water-insoluble enteric polymer during that period prior to the unacceptable increase of phthalic acid content.

When the pharmaceutical manufacturer is ready to use the powder for forming an enteric composition for coating tablets or the like, the powder is added to water, followed by the addition of a suitable plasticizer such as dibutyl-sebacate, diethyl phthalate, tributyl citrate, triglycerylacetate, propylene glycol or castor oil. The plasticizer is preferably used in an amount of between 10% and 40% by weight of the polymer. If desired, pigments, flavorings and/or preserving agents may also be added. Upon stirring, the aggregates break up to free the polymer particles in the form and near the size they had in the original dispersion.

The following is a specific example for carrying out the invention. 145 g of Myvacet ®9-40 was added to 1.3 liters (0.0013 $m^3$) of water, mixed for 30 minutes and passed through a Manton Gaulin homogenizer at 5500 psi (approximately 37.921 MPa) first stage, 500 psi (approximately 3.447 MPa) second stage, to form a stable aqueous emulsion. Myvacet 9-40 is a product of Eastman Chemical Company. It is a distilled acetylated monoglyceride which is a liquid at room temperature and has approximately 96% acetylation. 1,450 g of the Myvacet emulsion was mixed with 4,350 g of a 30% solids aqueous dispersion of cellulose acetate phthalate, mixed for 30 minutes and this mixture was homogenized first and second stage pressure settings as noted above and spray dried to form a powder. The aqueous dispersion of cellulose acetate phthalate comprised substantially spherical particles, substantially all of which had a diameter in the range of 0.2 to 0.5 μm. The spray drying was performed as follows: Dryer feed solids concentration of 25.08% was fed to a 3 foot (0.9144 m) Bowen spray dryer utilizing nozzle atomization, 0.01 inch (0.000254 m) opening. The slurry was fed to the dryer by means of a variable feed Moyno pump at a rate of 70 g per minute. Spray dryer air inlet/outlet temperature was operating at 150°/95° C. 1.9 pounds (approximately 0.86 Kg) of dry powder was collected per hour having an average moisture content of 2.1% and an average bulk density of 25.9 pounds per cu.ft. (approximately 414.78 kg/$m^3$). 306.44 g of the spray dried powder was added to 1.67 liters (0.00167 $m^3$) of water and mixed for 15 minutes with mild agitation. 67.5 g of diethyl phthalate was slowly added to the aqueous dispersion and mixed for 1 hour. The coating system so prepared was sprayed onto 2 kg of tumbling tablets in a 16 inch (0.4064 m) conventional coating pan apparatus utilizing intermittent spray by means of a Graco pump. Film coating on the tablets measured 7–8% based upon the dry weight of the tablet.

The tablets coated as above described were tested in accordance with U.S.P. XX enteric disintegration procedure. The tablets, which possessed a smooth elegant coating remained intact in water and gastric fluids and disintegrated in simulated intestinal fluids in about 15 minutes.

While the invention has been described specifically in connection with cellulose acetate phthalate, it will be apparent to those skilled in the art that it is equally applicable in principal to other known enteric polymers such as hydroxypropyl methylcellulose phthalate, polyvinyl acetate phthalate, and the like.

Having thus described the invention, what is claimed is:

1. A process of making a polymeric powder which is readily dispersible in water to provide a composition useful for forming an enteric coating on pharmaceutical dosage forms, comprising providing a freshly prepared aqueous dispersion of a water-insoluble enteric polymer, adding to said dispersion an acetylated monoglyceride characterized by being liquid at room temperature and having a degree of acetylation of at least about 96%, said acetylated monoglyceride being added in an amount of between about 6% and about 18% based upon the weight of the dry insoluble solids contained in the dispersion, thoroughly mixing to distribute the acetylated monoglyceride throughout the dispersion, and homogenizing and spray drying to form the powder.

2. The process set forth in claim 1 wherein the acetylated monoglyceride is added in an amount of between about 10% and about 14% based upon the weight of the dry insoluble solids contained in the dispersion.

3. The process set forth in claim 1 wherein the acetylated monoglyceride is pre-emulsified in water before being added to the dispersion.

4. The process set forth in claim 1 wherein said freshly prepared aqueous dispersion comprises substantially spherical particles predominately of a diameter below 5 μm.

5. The process set forth in claim 4 wherein said spherical particles predominately have a diameter between 0.2 and 0.5 μm.

6. The process set forth in claim 4 wherein the spray dried powder consists of aggregates of particles capable of being reconstituted to near the original size of the solid particles contained in the freshly prepared aqueous dispersion.

7. The process set forth in claim 6 comprising the additional steps of dispersing the spray dried powder in water, adding a plasticizer in an amount of between 10% and 40% of the weight of the polymer to form a coating composition and coating a pharmaceutical dosage form therewith.

8. A polymeric powder made by the process set forth in claim 1.

9. A process of making a polymeric powder which is readily dispersible in water to provide a composition useful for forming an enteric coating on pharmaceutical dosage forms, comprising providing a freshly prepared aqueous dispersion of cellulose acetate phthalate, adding to said dispersion an acetylated monoglyceride characterized by being liquid at room temperature and having a degree of acetylation of at least about 96%, said acetylated monoglyceride being added in an amount of between about 6% and about 18% based upon the weight of the dry insoluble solids contained in the dispersion, thoroughly mixing to distribute the acetylated monoglyceride throughout the dispersion, and homogenizing and spray drying to form the powder.

10. The process set forth in claim 9 wherein the acetylated monoglyceride is added in an amount of between about 10% and about 14% based upon the weight of the dry insoluble solids contained in the dispersion.

11. The process set forth in claim 9 wherein the acetylated monoglyceride is pre-emulsified in water before being added to the dispersion.

12. The process set forth in claim 9 wherein said freshly prepared aqueous dispersion comprises substantially spherical particles predominately of a diameter below 0.5 μm.

13. The process set forth in claim 12 wherein said spherical particles predominately have a diameter between 0.2 and 0.5 μm.

14. The process set forth in claim 12 wherein the spray dried powder consists of aggregates of particles capable of being reconstituted to near the original size of the solid particles contained in the freshly prepared aqueous dispersion.

15. The process set forth in claim 14 comprising the additional steps of dispersing the spray dried powder in water in the presence of a plasticizer in an amount of between 10% and 40% of the weight of the polymer to form a coating composition, and coating a pharmaceutical dosage form therewith.

16. A polymeric powder made by the process set forth in claim 9.

17. A polymeric powder capable of being readily dispersed in water to provide with the addition of a plasticizer a composition useful for forming an enteric coating on pharmaceutical dosage forms, said powder consisting essentially of a water-insoluble enteric polymer in the form of spherical polymer particles held together in aggregates and impregnated by an acetylated monoglyceride characterized by being liquid at room temperature and having a degree of acetylation of at least about 96%.

18. The polymeric powder set forth in claim 17 wherein said aggregates are capable of being reconstituted into polymer particles of a diameter less than 5.0 μm.

19. The polymeric powder set forth in claim 18 wherein said polymer particles are predominately of a diameter below 1.0 μm.

20. A polymeric powder capable of being readily dispersed in water to provide with the addition of a plasticizer a composition useful for forming an enteric coating on pharmaceutical dosage forms, said powder consisting essentially of substantially spherical particles of cellulose acetate phthalate held together in aggregates and impregnated by an acetylated monoglyceride characterized by being liquid at room temperature and having a degree of acetylation of at least about 96%.

21. The polymeric powder set forth in claim 20 wherein said polymer particles are predominately of a diameter less than 1.0 μm.

22. The polymeric powder set forth in claim 21 wherein said polymer particles are predominately of a diameter between 0.2 and 0.5 μm.

* * * * *